United States Patent [19]

Finney

[11] Patent Number: 5,282,795
[45] Date of Patent: Feb. 1, 1994

[54] PENILE RING IMPLANT AND METHOD

[75] Inventor: Roy P. Finney, Spring Hill, Fla.

[73] Assignee: Joseph E. Binard, Tampa, Fla.; a part interest

[21] Appl. No.: 30,987

[22] Filed: Mar. 12, 1993

[51] Int. Cl.⁵ .............................. A61F 5/44; A61F 2/02
[52] U.S. Cl. .................................... 604/351; 604/347; 604/353; 600/30
[58] Field of Search .................... 600/40, 41, 30; 604/347, 348, 351, 353; 623/11; 128/767, 885, 898, 899

[56] References Cited

U.S. PATENT DOCUMENTS

| | | | |
|---|---|---|---|
| 3,773,040 | 11/1973 | Gavrilovich | 600/41 |
| 4,381,767 | 5/1983 | Finney | 600/40 |
| 4,387,705 | 6/1983 | Finney | 600/40 |
| 5,027,800 | 7/1991 | Rowland | 600/39 |

Primary Examiner—Gene Mancene
Assistant Examiner—Cindy A. Cherichetti
Attorney, Agent, or Firm—Quarles & Brady

[57] ABSTRACT

A penile ring implant of soft biocompatible material is formed in situ and implanted beneath the skin of the penis of an incontinent male by use of a rod and a probe to form a protuberance which permits the patient to securely attach and easily remove the flexible sheath of the urinary collection device without the assistance of others. A kit for forming and implanting the ring implant includes an elongated D-shaped soft rod, a malleable probe and a connector.

4 Claims, 2 Drawing Sheets

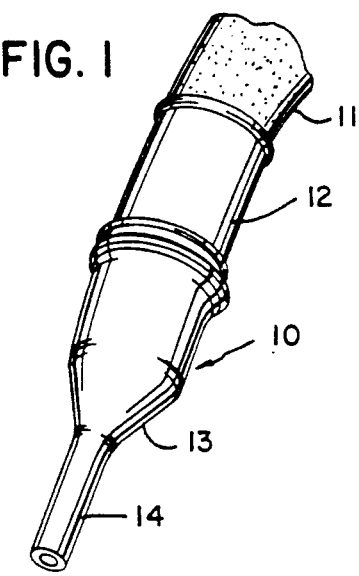
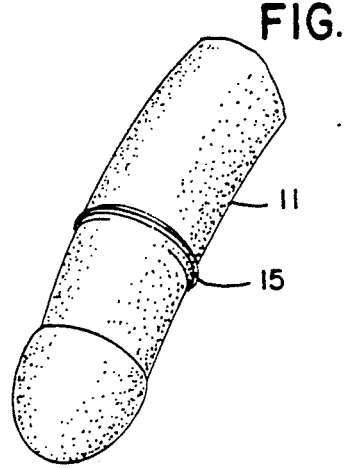
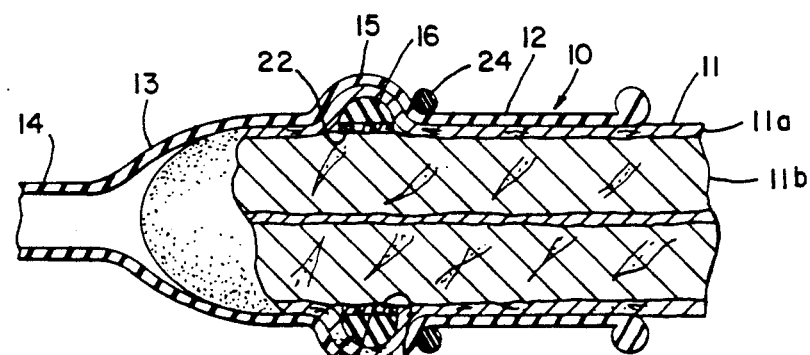
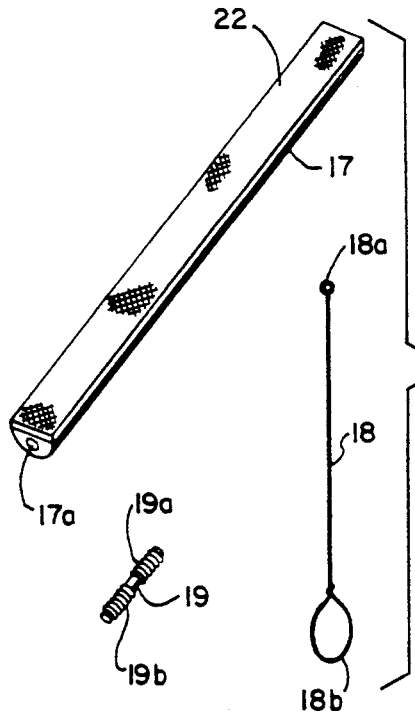

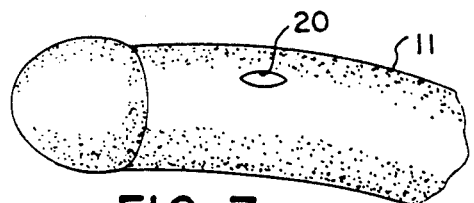
FIG. 7
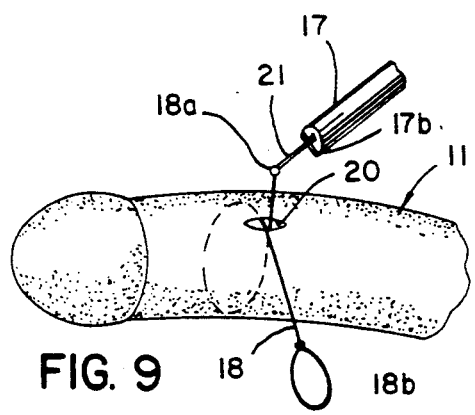
FIG. 9
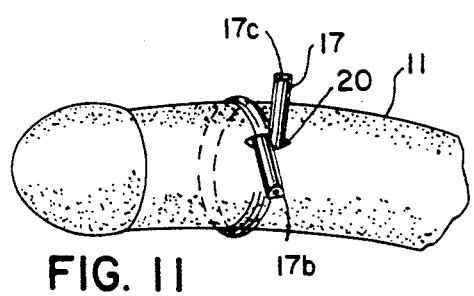
FIG. 11
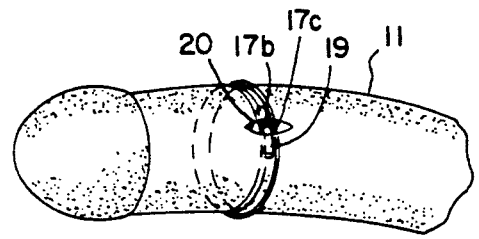
FIG. 13
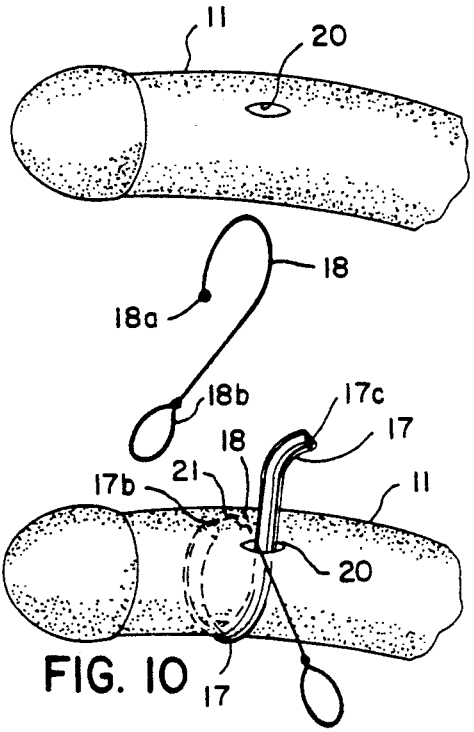
FIG. 8
FIG. 10
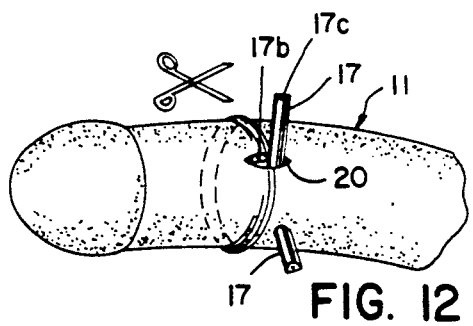
FIG. 12
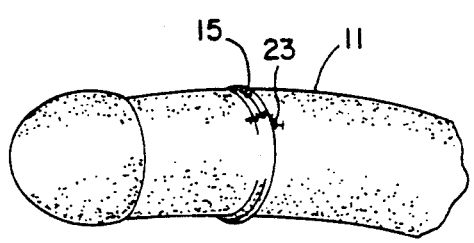
FIG. 14

PENILE RING IMPLANT AND METHOD

RELATED CASES

This application is based on my Disclosure Document No. 277,538 filed Mar. 26, 1991.

FIELD OF THE INVENTION

The present invention relates to a penile implant and more particularly to a penile ring implant which is useful in retaining the flexible sheath of a urinal device in place on the penis of an incontinent male patient. It also states a simplified method of implanting the penile ring.

BACKGROUND OF THE INVENTION

Incontinent male patients, such as those suffering from spinal cord injuries, often wear devices for the collection of urine. The urinary collection device most widely used with incontinent male patients is commonly called a "Texas Catheter" and it consists of a flexible condom-like sheath which is secured to the patient's penis and a tubular member which connects the condom-like device to a suitable urine receptacle. A device of this type is shown in the Rogers et al U.S. Pat. No. 3,835,857, granted Sep. 17, 1974.

One of the problems involved in the use of the "Texas Catheter" is that the sheath which depends upon its elasticity to stay in place can be accidently removed quite easily from the patient's penis without the patient being aware of its removal. Another Rogers et al patent, U.S. Pat. No. 3,863,638, discloses a liner pad which has an adhesive coating which clings to the penis and which is designed to retain the elastic sheath on the penis. Still another patent relating to a sheath liner useful for this purpose is U.S. Pat. No. 4,187,851.

Although the use of an adhesive coated sheath liner is an improvement on the use of the sheath itself in preventing accidental removal, it is not without disadvantages. For example, the liner normally has to be either placed on or removed from the penis of the patient by a person other than the patient. In addition, the liner and its adhesive layer can cause tissue irritation.

In my earlier U.S. Pat. Nos. 4,381,767 and 4,387,705, I disclosed implantable rings which can be implanted under the penile skin to form a outwardly extending, circumferential protuberance that assists in retaining a Texas Catheter in place. Although both of these patented devices are useful, they do require making a circumcision type incision completely about the penile shaft.

Obviously, it would be advantageous to have an improved ring and a simplified method for implanting a ring to more securely attach the sheath of a Texas Catheter to the penis of an incontinent male patient.

SUMMARY OF THE PRESENT INVENTION

It is an object of the present invention to disclose an improved penile ring implant which can be more simply surgically implanted to provide a superior permanent means of retaining the flexible sheath of a urinary collection device in place.

It is another object of the present invention to disclose a novel method for implanting the improved penile ring implant in a penis for retaining the sheath of a urinary collection device upon the penis of an incontinent male patient.

It also is an object to disclose a kit for forming and implanting the penile ring implant of the present invention.

The penile ring implant of the present invention is a ring of soft, flexible, biocompatible material which is implanted underneath the penile skin of the distal end of the patient's penis. The ring preferably is D-shaped in cross section and it is implanted with the curved belly of the D extending outwardly. The ring preferably is formed in situ from a D-shaped, elongated, trimmable, soft rod of biocompatible material and a connector for joining the ends of rod and retaining the rod in the form of a ring.

The simplified method of forming and implanting the penile ring in the penis of a male comprises making a small incision in the skin of the penis covering the tunica albuginea of the penis; introducing and working one end of a malleable probe circumferentially about the penis between the skin and the tunica albuginea until that one end of the probe exists from the incision; attaching to that one end of the probe one end of an elongated soft, flexible rod; pulling the one end of the probe with the rod attached back through the incision around the penis and out the incision so that the main body of elongated rod is positioned between the skin and the tunica albuginea completely encircling the penis and both ends of the rod extend out of the incision; trimming at least one end of the rod, if necessary, so that the two ends of the rod when approximated form a ring having an inner surface contacting the tunica albuginea; joining the two ends of the rod to form a unitary ring implant in situ which forms a sheath retaining protuberance; and then closing said incision.

In the preferred method the two ends of the rod are joined with a connector.

These and still other objects and advantages of the invention will become apparent to those skilled in the art from the description and the drawings which follow.

BRIEF DESCRIPTION OF THE DRAWINGS

In the Drawing:

FIG. 1 is a perspective view of a penis with a penile ring implant of the present invention surgically implanted and a sheath of a urinary collection device in place;

FIG. 2 is a perspective view of a penis with the penile ring implanted therein but without the sheath;

FIG. 3 is a partial sectional top plan view taken along the line 3—3 in FIG. 1;

FIG. 4 is a perspective view, partly in section, of an elongated rod of biocompatible material, a probe and a connector for use in forming the rod into a penile ring;

FIG. 5 is a cross sectional view of the ring taken along line 5—5 in FIG. 4;

FIG. 6 is an enlarged sectional view of a portion of the ring implant including the connector and the connector by itself; and FIGS. 7 to 14 are schematic views showing the preferred method of the present invention for forming and implanting the ring implant.

DESCRIPTION OF THE PREFERRED EMBODIMENT

Referring to FIG. 1, a sheath 10 of a urinary collection device is shown in position upon a penis 11. The sheath 10 has a body portion 12 joined to a conical funnel like section 13 which terminates in a tube 14 which leads to a urine receptacle (not shown). The body portion 12 is of a very thin elastic material such as latex rubber which is capable of being rolled upon itself and then unrolled onto the penis 11 over a protuberance 15. Referring to FIG. 2, the penis 11 with the protuberance 15 is seen with the sheath 10 removed. As seen best in FIG. 3, the protuberance 15 is formed by a ring implant 16 implanted under the skin 11a of the penis 11.

Turning to FIG. 3 it can be seen that the penile ring implant 16 which is made of a physiologically inert material, such as medical grade silicone rubber, is implanted under the penile skin 11a above the corpora 11b of the penis 11 adjacent the distal end of the penis. The ring 16 is D-shaped in cross section as seen in FIG. 5 and it is implanted as seen in FIG. 3 with the fabric lined base 16a towards the penile shaft and the belly 16b of the D extending outwardly.

Referring to FIG. 4, there can be seen the components of a kit comprising an elongated D-shaped rod 17 from which the ring implant 16 is made, a malleable metal probe 18 for moving the rod 17 into position circumferentially about the penis and a flanged connector 19 for connecting the ends of the rod 17 after they have been trimmed, if necessary, into the ring implant 16. As seen best in FIG. 6, the connector 19 is of a flexible, stiffer material than the ring 16 and smaller in diameter so that the ends 19a and 19b of connector can be forced into the lumen 17a of the approximated ends of the rod 17 to form the ring implant 16.

In place of the connector 19, which can take various forms, the ends 17b and 17c of the rod 17 can be mitered, formed into a ring implant with the belly 16b of the D extending outwardly and the ends 17b and 17c bonded together by use of a suitable adhesive or by other acceptable means.

Medical grade silicone rubber is the preferred material for the ring implant 16 and the connector 19 because it is biocompatible and it can be formulated to provide a material which possesses suitable tensile strength, stiffness and softness for the intended function. However, other materials possessing the desired properties also may be used.

The stiffness or softness of the material may be measured with a durometer, such as a Shore A durometer, which ascertains the depth of the penetration of a specified indentor into a specimen under specified conditions. A scale is chosen so that zero represents a material showing no measurable resistance to indentation and 100 represents a material showing no measurable indentation.

Tensile strength is the unit stress which produces failure of a specimen in tension. A Scott Tensile Tester may be used to measure the stress which produces failure In order to minimize the possibility of its erosion through the penile skin, the ring implant 16 is preferably formed of a material having a Shore A hardness of about 10 which is very soft and flexible and all edges are arced or curved. The connector 19 is of a relatively stiffer but still flexible material. If the patient is impotent, a pair of composite penile rod implants of the type disclosed in U.S. Pat. No. 4,066,037 also can be implanted.

The preferred method of forming the ring implant in situ and implanting it will now be described in connection with FIGS. 7 to 14.

As seen in FIGS. 7 and 8 a small incision 20 (about 0.5 centimeters long) is made in the skin of the penis covering the tunica albuginea. One end 18a of the malleable probe 18 is then introduced and worked circumferentially about the penis between the skin and the tunica albuginea using the other end 18b as a handle until the first end 18a of the probe exits from the incision 20. The end 17b of the elongated soft, flexible trimmable, D-shaped rod 17 is then attached to the loop at the first end 18a of the probe 18 with a suture 21 (FIG. 9). Next by pulling outwardly on the other end 18b of the probe 18 the end 18a with the rod 17 attached is pulled through the incision 20 and around the penis and out the incision 20 (FIGS. 10 and 11). As a result, the main body of elongated rod is now positioned between the skin and the tunica albuginea completely encircling the penis and both ends 17b, 17c of the rod 17 extend out of the incision 20 (FIG. 11). If necessary at least one end of the rod 17 is trimmed (FIG. 12) so that the two ends 17b, 17c of the rod 17 can be approximated to form a ring having its base contacting the tunica albuginea. The two ends 17a, 17b of the rod 17 are then joined by inserting one end 19a of the flanged connector 19 into the lumen 17a of one end 17b of the rod 17 and the other end 19b into the lumen 17a of the other end 17c to form the unitary ring implant 16 (FIGS. 6 and 13) which forms the sheath retaining protuberance 15 seen in FIGS. 1 and 14. The incision 20 is then closed with sutures 23 (FIG. 14).

The fabric 22 on the underside of the base of the ring 16 (seen in FIGS. 3–5), provides a surface for tissue ingrowth which can help anchor the ring implant 16 in place. The fabric 22 can be either a solid piece or intermittent strips. The intermittent strips are preferred because they are less likely to constrict the blood supply or prevent the ring from expanding.

Referring back to FIG. 3 it can be seen that an elastic band 24 can be placed on the penis 11 over the sheath 10 behind the protuberance formed by the ring implant 16 to further secure the sheath 10 in place. If desired, the elastic band 24 can be molded in as an integral part of the sheath 10.

It will be apparent to those skilled in the art that use of the ring implant of the present invention and the simplified method provide significant advantages over the previous methods of attaching the flexible elastic sheath of the urinary collection device to the penis. Prior art techniques are generally temporary and/or potentially unsanitary and/or require the assistance of others for proper placement of the sheath on the penis. In contrast, a patient with a ring implant of the present invention can simply and readily attach the condom-like sheath to his penis by himself by unrolling the prerolled sheath over the distal end of the penis and the protuberance 15 formed by the implanted ring (as seen in FIG. 1). The protuberance 15 formed by the implant 16 increases the diameter of the penis and provides a very effective means of retaining the sheath in place. In place of the elastic band 24, other means, such as adhesive tape (not shown) also can be used to help secure the sheath in place.

It is to be understood that the foregoing description has been for purposes of illustration and that a number of modifications and changes may be made without departing from the spirit and scope of the present invention. For example, if desired, in place of the fabric 22 one or more porous patches may be attached to the ring to permit tissue ingrowth to help anchor it in place. Therefore, the invention is not to be limited by any of the specific embodiments described but only by the claims which follow:

I claim:

1. A method of forming a sheath retaining annular protuberance in the penis of a male which comprises:
   (a) making a small incision in the skin of the penis covering the tunica albuginea of the penis;
   (b) introducing and working one end of a malleable probe circumferentially about the penis between the skin and the tunica albuginea until that one end of the probe exits from the incision;
   (c) attaching to that one end of the probe one end of an elongated soft, flexible rod;
   (d) pulling the one end of the probe with the rod attached back through the incision around the penis and out the incision so that the main body of elongated rod is positioned between the skin and the tunica albuginea completely encircling the penis and both ends of the rod extend out of the incision;
   (e) trimming at least one end of the rod, if necessary, so that the two ends of the rod when approximated form a ring having an inner surface contacting the tunica albuginea;
   (f) joining the two ends of the rod to form a unitary ring which forms a sheath retaining protuberance; and
   (g) then closing said incision.

2. A method of claim 1 in which the two end of the rod are joined with a flanged connector.

3. A method of claim 1 in which the elongated rod has a generally D-shaped cross-section.

4. A kit for implanting a ring under the skin of a penis to form a sheath-retaining protuberance, said kit comprising:
   (a) an elongated, soft, trimmable, flexible rod which is longer than needed to completely encircle the penis circumferentially.
   (b) a malleable probe which is longer than needed to encircle the penis circumferentially and which has a loop at one end for attachment with a suture to the rod and a handle at the other end so that the probe can be introduced into a small incision in the skin of the penis, maneuvered circumferentially about the penis below the skin, attached to the loop of the rod and used to pull the rod into position about the penis; and
   (c) connector means for joining the ends of the rod to form a ring when they have been trimmed to the proper length; if necessary, to circumferentially encircle the penis.

* * * * *